(12) United States Patent
Sjögren et al.

(10) Patent No.: US 6,503,266 B1
(45) Date of Patent: Jan. 7, 2003

(54) INFLATABLE HEMOSTAT HAVING REINFORCED PORTION

(75) Inventors: Iwar Sjögren, Falun (SE); Per Egnelöv, Uppsala (SE); Dan Akerfeldt, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 09/355,736
(22) PCT Filed: Feb. 7, 1997
(86) PCT No.: PCT/SE97/00188
§ 371 (c)(1),
(2), (4) Date: Oct. 21, 1999
(87) PCT Pub. No.: WO98/34547
PCT Pub. Date: Aug. 13, 1998
(51) Int. Cl.⁷ .................................................. A61F 5/34
(52) U.S. Cl. ......................................... 606/201; 602/13
(58) Field of Search .................................. 606/201–204, 606/204.15, 204.25, 204.35, 204.45, 204.55, 157; 600/490, 499, 481; 602/13, 53

(56) References Cited

U.S. PATENT DOCUMENTS

| | | | | |
|---|---|---|---|---|
| 2,344,021 A | * | 3/1944 | Bouziane | 606/201 |
| 3,171,410 A | * | 3/1965 | Towle, Jr. et al. | 606/201 |
| 4,049,854 A | * | 9/1977 | Casey et al. | 428/72 |
| 4,175,562 A | * | 11/1979 | Honan | 606/202 |
| 5,234,459 A | * | 8/1993 | Lee | 606/202 |
| 5,433,724 A | * | 7/1995 | Kawasaki et al. | 606/202 |
| 5,542,427 A | | 8/1996 | Akerfeldt | |
| 5,643,315 A | * | 7/1997 | Daneshvar | 606/201 |
| 5,968,072 A | * | 10/1999 | Hite et al. | 606/202 |
| 5,997,564 A | * | 12/1999 | Shehata et al. | 606/201 |

FOREIGN PATENT DOCUMENTS

| | | |
|---|---|---|
| EP | 462088 | 12/1991 |
| WO | PCT/SE93/00705 | 8/1993 |
| WO | 9702783 | 1/1997 |

* cited by examiner

Primary Examiner—Nicholas D. Lucchesi
Assistant Examiner—David C. Comstock
(74) Attorney, Agent, or Firm—Foley & Lardner

(57) ABSTRACT

The invention relates to an air cushion unit (2) of single use type for stopping bleeding. The unit (2) comprises a base plate (4) and an inflatable air cushion (8) attached to the base plate (4). The air cushion (8) comprises a reinforced portion (16), integral with the cushion surface, and extending radially along the inside of the cushion, and corresponding to an area of contact with a wound site.

18 Claims, 3 Drawing Sheets

INFLATABLE HEMOSTAT HAVING REINFORCED PORTION

TECHNICAL FIELD OF THE INVENTION

The present invention relates to air cushion units for stopping bleeding at wounds after arterial puncture.

BACKGROUND OF THE INVENTION

This invention is an improvement of the devices disclosed in PCT/SE93/00705 and U.S. Pat. No. 5,542,427.

The replaceable unit according to these disclosures, which is for single use, includes a base plate, the upper side of which is attached to the arch of a femoral compressor, such as the one disclosed in EP-0 462 088, assigned to the present applicant. The attaching is done by means of a "snap attachment".

On the base plate there is an inflatable air cushion which is mounted by gluing or fusing along the base plate's periphery. The material which the cushion is made of is, seen from a cross sectional view, folded so that the air cushion when not inflated, that is, as it is packaged, takes up as little volume as possible.

Along the periphery of the base plate there is a groove. Melt-glue is placed in the groove and after heat and pressure treatment in a manner well known to the skilled person, this makes for an airtight sealing of the air cushion against the base plate.

A problem with the prior art air cushion units is that they do not exert the desired centered and axially directed pressure during the entire pressure treatment. Especially during the pressurising and depressurising phases, it may happen that one of the folds in the air cushion forms a circular rim extending beyond the contact surface. Also, during pressurising and depressurising the top portion of the cushion may invert and thereby exerts less pressure in the central compression area. These phenomena causes the entire unit to press not on the wound but instead on a circular path around the wound. This obviously may cause unnecessary bleeding, since there is nothing pressing properly against the wound, or at least not to a sufficient extent. It may also happen that it is no longer possible to actually be able to pressurise the cushion sufficiently to obtain the necessary contact at the wound, in that the cushion does not expand any further. In such circumstances the entire device may be rendered at least partially ineffective.

SUMMARY OF THE INVENTION

An object of the present invention is therefore to provide an improved air cushion unit, that sits steadily on the wound site and as desired, exerts a centered and axially directed pressure during the entire compression period, such that the risk of inverting of the cushion is eliminated. Also, the risk for rebleeding should be eliminated.

This object is achieved by providing an air cushion unit, preferably of a single use type, for use together with a femoral compressor. The air cushion unit, which is attached to the arch of the femoral compressor, has a base plate and an inflatable air cushion attached to the base plate. The air cushion is characterised by being reinforced over an area of contact against a wound site.

Preferably said reinforcement is achieved by providing reinforcement elements in the form of ribs or ridges in a star configuration on the inside of the air cushion, supporting the entire area of contact.

In a particularly preferred embodiment said reinforcement elements have a shape corresponding to a circular segment and are laid out in a star configuration.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will become more fully understood from the detailed description given hereinbelow and the accompanying drawings which are given by way of illustration only, and thus not limitative of the present invention, and wherein FIG. 1 is a cross sectional view of a prior art air cushion unit;

FIG. 3b is a cross section along the line b—b in FIG. 3a;

DETAILED DESCRIPTION OF PREFERRED EMBODIMENTS AND BEST MODE

Figure 1:
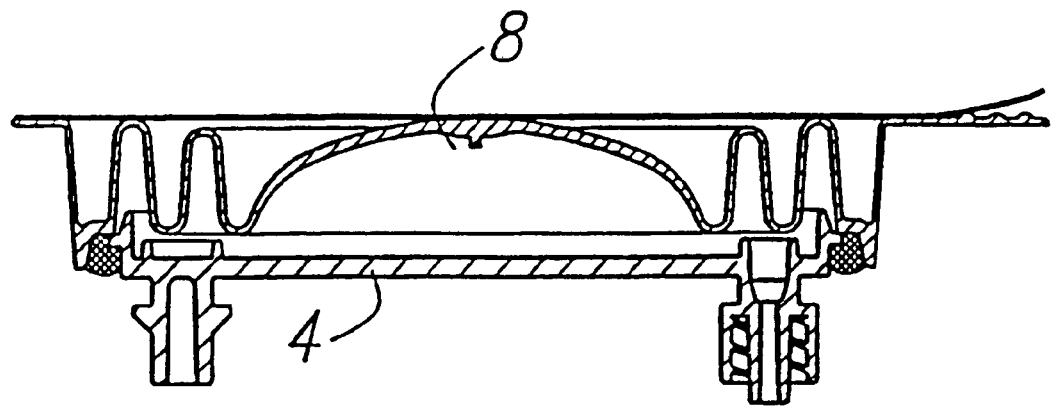

The air cushion unit according to the present invention has the same basic design as the one disclosed in the above referenced PCT/SE93/00705. The prior art pad is shown in FIG. 1.

The replaceable unit according to these disclosures, which is for single use, includes a base plate 4, the upper side of which is applied to a femoral compressor. The application to the femoral compressor is done by means of a "snap attachment".

On the base plate there is an inflatable air cushion 8 which is mounted by gluing or fusing along the base plate's periphery. The material which the cushion is made of is, seen from a cross sectional view, folded so that the air cushion when not inflated, that is, as it is packaged, takes up as little volume as possible.

Figure 2:
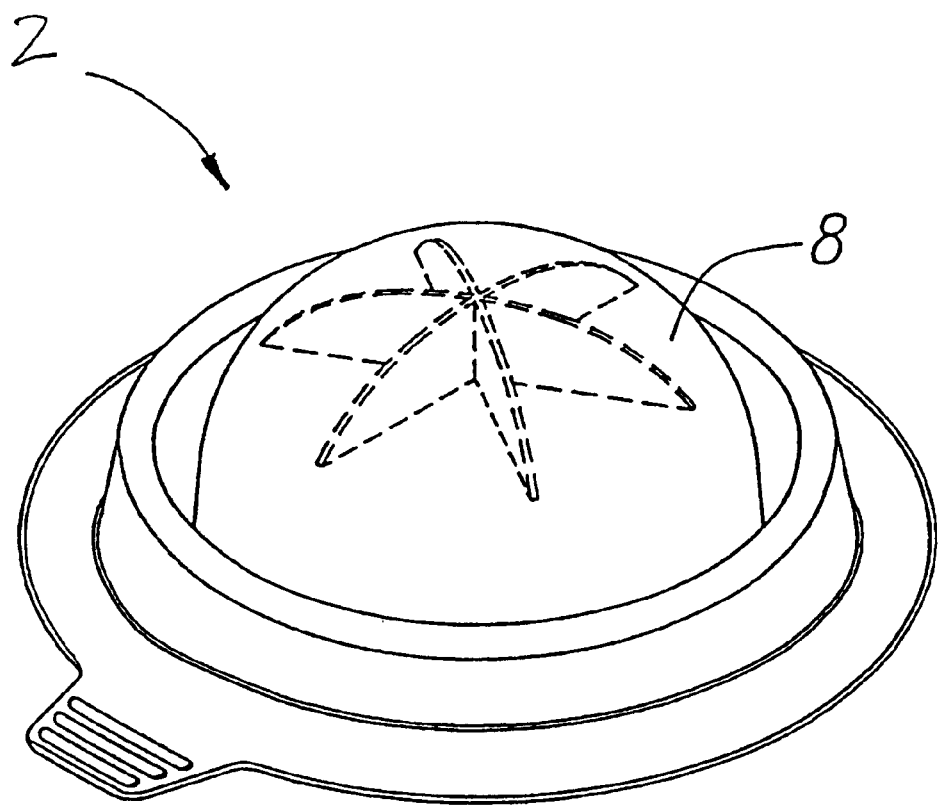
FIG. 2 is a perspective view of a air cushion unit according to the invention.
Figure 3B:
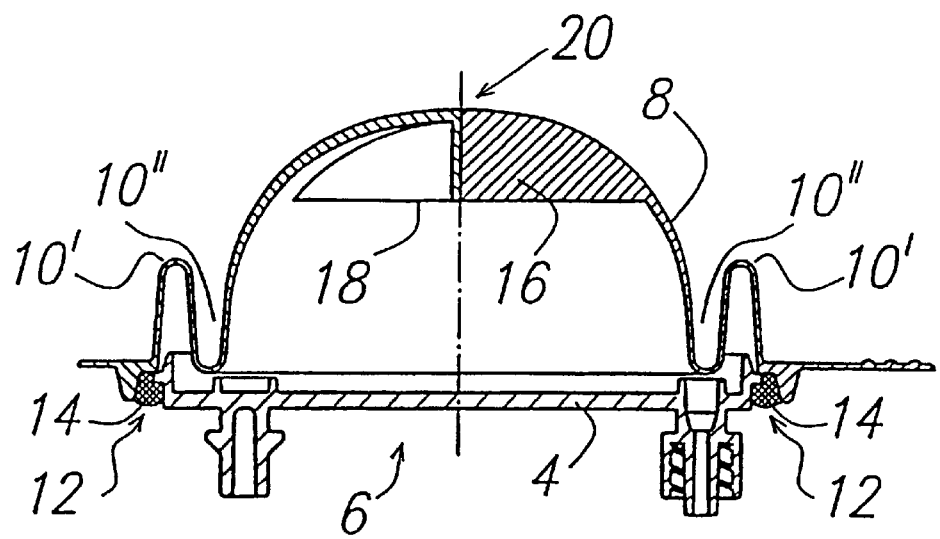
Figure 3A:
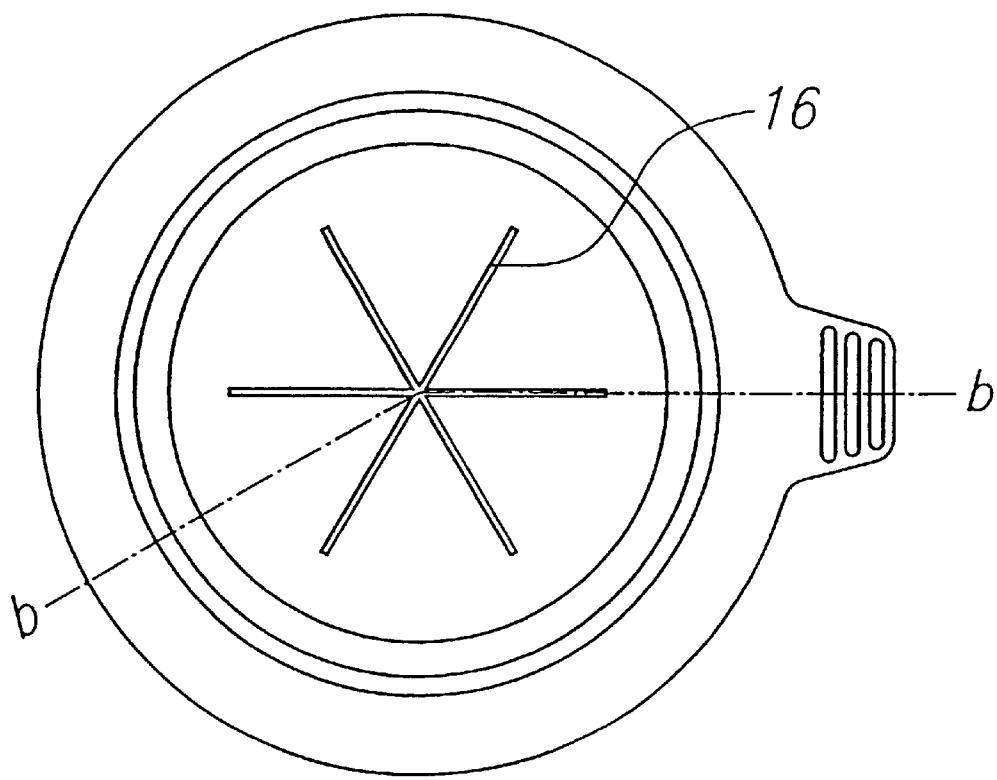
FIG. 3a is a top view of a preferred embodiment of the invention.

Turning now to FIGS. 2 and 3a–3b, the air cushion unit according to the invention, a single use replaceable unit, generally shown in FIG. 2, is designated with the reference number 2, and, includes a base plate 4 (see FIG. 3b), the upper (when installed on a patient) side 6 of which is adapted to be attached to the arch of a femoral compressor, such as the one disclosed in applicant's European Patent Application EP-0 462 088. The attachment of the pad to the femoral compressor is done by means of a "snap attachment", which is fully disclosed in above mentioned application PCT/SE93/00705, and will therefore not be described herein.

On the base plate there is provided an inflatable air cushion 8 (to be described in detail) which is mounted by methods such as gluing, welding or fusing along the base plate's 4 periphery.

The material from which the cushion is made is folded 10', 10" at the periphery so that the air cushion 8 when not inflated, that is, as it is packaged, takes up as little volume as possible.

Along the periphery of the base plate there is a groove 12; melt-glue 14 is placed in the groove and after heat and pressure treatment in manner well known to the skilled person, and this ensures an airtight sealing of the air cushion 8 against the base plate 4.

The novel feature of the air cushion unit according to the present invention is the design of the cushion, and will now be described in further detail with reference to FIGS. 3a and 3b, illustrating an at present preferred embodiment of the invention.

As can be seen in FIG. 3b, the uninflated position of the air cushion 8 differs from the prior art device in the same uninflated state, in that in the prior device, the surface of contact on the cushion is essentially flush with the folds, such that the overall shape of an uninflated prior art device is a generally flat, or disc shaped structure.

The cushion 8 of the invention on the other hand, has a more rigid structure, such that the top hemispherical portion will not be foldable, but extends beyond the rim like fold 10'.

The novel device comprises reinforcement ribs or ridges 16 inside the cushion, rendering it relatively rigid, such that it is not possible to fold it more than in one fold. Said ribs or ridges are integral with the cushion surface, and for the purpose of this application, the term "integral" has the meaning that the reinforcements and the cushion form a unitary piece in the finished state. As will be explained, the ridges may be made in the same operation as the cushion is made, or they may be separately attached. They are regarded as "integral" with the cushion regardless of how they are made.

In the at present preferred embodiment the reinforcement ribs or ridges 16 have the general shape of a circular segment, i.e. the geometrical shape being that of the area of a circle, delimited by a chord. The "chord segments" are arranged to pass through each other, thereby forming a star configuration. The number of segments can vary from two and upwards, the preferred number being three at present, thus forming a star with six beams (see FIG. 3a).

Also the width in vertical direction of the segments may vary. In the embodiment shown in FIGS. 3 and 4, the lower edge 18 of each segment is a straight line (i.e. corresponding to a chord) at an elevation of about one third of the distance from the top 20 of the cushion 8. However, in principle this lower edge may extend all the way down to the base plate.

It should also be understood that the lower edge of the segments not necessarily need to be a straight line, but could have a curved contour such as to have the maximum width at the uppermost portion and approach the inner surface of the cushion nearer the base plate.

Figure 4:
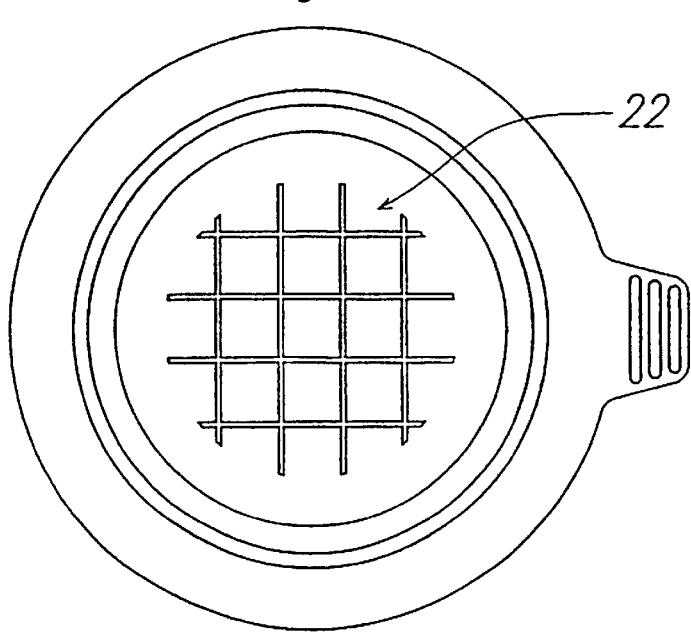
FIG. 4 is a top view of an alternative embodiment of the invention.

In another possible embodiment, the ribs form a grid like structure 22. This structure may be a square grid as shown in FIG. 4. Other shapes such as rectangular or honey-combs are conceivable and falls within the scope of the inventive idea.

Figure 5:
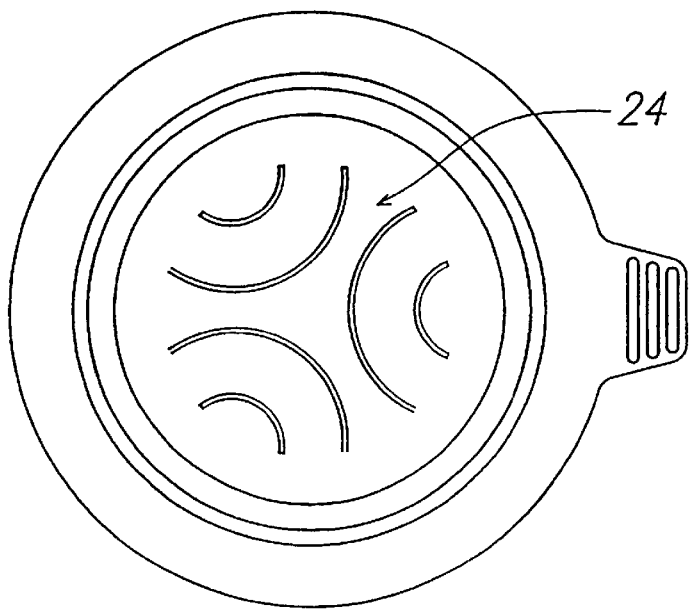
FIG. 5 is a top view of another embodiment of the invention.

FIG. 5 illustrates still another way of reinforcing the cushion embodying the invention, in a top view. Here the reinforcement ridges 24 are curved structures, like portions of cylinders, adapted to fit inside and against the inner surface of the cushion.

Figure 6:
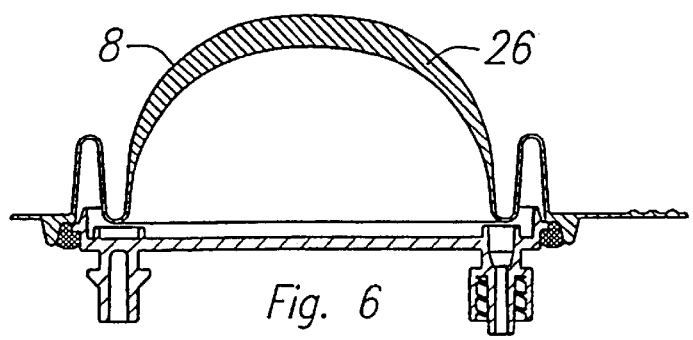
FIG. 6 is a cross section section through an alternative embodiment of the reinforcement portion.

In an additional embodiment, showm in FIG. 6, the desired stiffness is achieved by providing more material in that portion 26 of the cushion 8 forming the contact surface. Thus, the thickness of the cushion 8 is larger in this area.

The air cushion of the invention is preferably made by injection moulding to make the entire cushion in one manufacturing operation. It is of course conceivable to make the reinforcement structures separately and attach them inside the cushion in a separate step, although this of course is more time consuming and costly. If it for some reason is necessary to make the reinforcements of another material, the latter is of course unavoidable. The material of the cushion is preferably transparent to enable inspection of the wound through the unit.

Likewise it is conceivable and within the scope of the inventive idea to attach a separate reinforcment structure to the outer surface of the cushion. In the latter case of course the reinforcment must have a smooth surface in order not to cause discomfort to the patient.

Assembly of an entire air cushion unit is done exactly as with the prior art device and will not be discussed herein.

In order to protect the air cushion from contamination, obviously the simple removable flat lid according to the previously mentioned PCT/SE93/00705, is not applicable. However, the same basic principle is used, in that there will be a removable cap or cover, attached at the base plate in the same way as with the prior art device, i.e. by fusing it against the circumference of said base plate.

The invention being thus described, it will be clear that the same may be varied in many ways. Such variations are not to be regarded as a departure from the spirit and scope of the invention, and all such modifications as would be obvious to one skilled in the art are intended to be included within the scope of the following claims.

What is claimed is:

1. An air cushion unit comprising:
a base plate and an inflatable air cushion attached to the base plate, wherein said air cushion includes a reinforced portion, integral with a cushion surface, said reinforced portion corresponding to an area of contact with a wound site, and wherein the reinforced portion comprises reinforcement elements extending radially along the inside of the cushion.

2. The air cushion unit of claim 1, wherein the reforced portion comprises an area of increased material thickness.

3. A femoral compressor comprising an air cushion unit as claimed in claim 1.

4. An air cushion unit, comprising:
a base plate and an inflatable air cushion attached to the base plate, wherein said air cushion includes a reinforced portion, integral with a cushion surface, said reinforced portion corresponding to an area of contact with a wound site, wherein the reinforced portion comprises reinforcement elements extending radially along the inside of the cushion and wherein the reinforcement elements include at least two circular segments in a star configuration.

5. An air cushion unit, comprising:
a base plate and an inflatable air cushion attached to the base plate, wherein said air cushion includes a reinforced portion, integral with a cushion surface, said reinforced portion corresponding to an area of contact with a wound site, wherein the reinforced portion comprises reinforcement elements extending radially along the inside of the cushion and wherein the reinforcement elements include at least three circular segments in a star configuration.

6. An air cushion unit, comprising:
a base plate and an inflatable air cushion attached to the base plate, wherein said air cushion includes a reinforced portion, integral with a cushion surface, said reinforced portion corresponding to an area of contact with a wound site, and wherein the reinforced portion comprises a grid like structure.

7. An air cushion unit, comprising:

a base plate and an inflatable air cushion attached to the base plate, wherein said air cushion includes a reinforced portion, integral with a cushion surface, said reinforced portion corresponding to an area of contact with a wound site, wherein the reinforced portion comprises a grid like structure, and wherein the grid like structure is in the form of a honey-comb grid.

8. An air cushion unit, comprising:

a base plate and an inflatable air cushion attached to the base plate, wherein said air cushion includes a reinforced portion, integral with a cushion surface, said reinforced portion corresponding to an area of contact with a wound site, wherein the reinforced portion comprises a grid like structure, and wherein the grid like structure is in the form of a checker grid.

9. An air cushion unit, comprising:

a base plate and an inflatable air cushion attached to the base plate, wherein said air cushion includes a reinforced portion, integral with a cushion surface, said reinforced portion corresponding to an area of contact with a wound site, wherein the reinforced portion comprises reinforcement elements extending radially along the inside of the cushion, and wherein said reinforced portion is separately made and attached to the inner surface of the cushion.

10. An air cushion unit, comprising:

a base plate and an inflatable air cushion attached to the base plate wherein said air cushion includes a reinforced portion, integral with a cushion surface, said reinforced portion corresponding to an area of contact with a wound site, wherein the reinforced portion comprises reinforcement elements extending radially along the inside of the cushion and wherein the reinforcement elements include at least two circular segments in a star configuration wherein said reinforced portion is separately made and attached to the outer surface of the cushion.

11. The air cushion unit of claim 10, further comprising an additional contact surface on said reinforced portion to provide for smooth contact.

12. An air cushion unit connectable to an arch of a femoral compressor, said unit comprising:

i) a base plate provided with snap-fit fasteners for attachment to said arch of said femoral compressor;

ii) an inflatable air cushion attached to the base plate at a peripheral portion of said base plate;

iii) an inlet integral with said base plate, to inflate said air cushion;

iv) an outlet, to depressurize the air cushion;

wherein said air cushion in its uninflated state is circumferentially folded at its peripheral portion; and wherein said air cushion is reinforced over a portion thereof covering an area corresponding to a wound site over which the cushion is applied, the reinforcement portion comprising reinforcement elements extending radially along the inside of said cushion.

13. A method of applying a controlled, axially directed and centered pressure on a wound site after arterial puncture, comprising a) providing an air cushion unit at said wound site, the air cushion unit comprising an inflatable air cushion, the air cushion having a reinforced portion having reinforcement elements extending radially along the inside of the cushion, integral with the cushion, said reinforced portion corresponding at least to an area of contact covering the wound; and b) inflating said air cushion to successively increase the pressure in said cushion, thereby increasing the pressure on said wound, whereby said controlled, axially directed and centered pressure is achieved by virtue of said reinforced portion of said cushion.

14. An air cushion unit comprising:

an inflatable air cushion wherein said air cushion includes a reinforced portion integral with a cushion surface, said reinforced portion corresponding to an area of contact with a wound site, and wherein the reinforced portion includes reinforcement elements extending radially along the inside of the cushion.

15. The air cushion unit of claim 14, wherein at least one reinforcement element substantially corresponds to a center of the reinforced portion.

16. An air cushion unit comprising:

an inflatable air cushion including a reinforced portion integral with a cushion surface, said reinforced portion corresponding to an area of contact with a wound site and including at least one reinforcement line, located inside the air cushion, that provides radial reinforcement.

17. An air cushion unit, comprising:

a base plate and an inflatable air cushion attached to the base plate, wherein said air cushion includes a reinforced portion, said reinforced portion corresponding to an area of contact with a wound site, and wherein the reinforced portion comprises reinforcement elements extending radially along the inside of the cushion.

18. An air cushion unit, comprising:

a base plate and an inflatable air cushion attached to the base plate, wherein said air cushion includes a reinforced portion, said reinforced portion corresponding to an area of contact with a wound site, and wherein the reinforced portion comprises reinforcement elements configured to provide a centered and axially directed pressure on the wound site.

* * * * *